United States Patent [19]

Gerstmann et al.

[11] Patent Number: 4,502,626

[45] Date of Patent: Mar. 5, 1985

[54] COMBUSTION PRODUCT CONDENSING WATER HEATER

[75] Inventors: Joseph Gerstmann, Framingham; Andrew D. Vasilakis, Bedford, both of Mass.

[73] Assignee: Gas Research Institute, Chicago, Ill.

[21] Appl. No.: 448,033

[22] Filed: Dec. 8, 1982

Related U.S. Application Data

[63] Continuation-in-part of Ser. No. 150,289, May 16, 1980, Pat. No. 4,403,572.

[51] Int. Cl.³ .............................................. F23N 1/08
[52] U.S. Cl. .................................. 236/20 R; 165/12 S; 165/DIG. 18; 165/160; 122/20 B; 122/33; 126/350 R
[58] Field of Search ............... 237/19, 8 R; 122/20 B, 122/33, 32; 165/DIG. 2, DIG. 12, 163, 161, 160, DIG. 18; 126/427, 350, 365; 236/20 R; 431/242, 243

[56] References Cited

U.S. PATENT DOCUMENTS 2,937,625  5/1960  Meyers ................................ 122/33

FOREIGN PATENT DOCUMENTS

30162    7/1884   Fed. Rep. of Germany.
1907987  9/1970   Fed. Rep. of Germany.
3041265  9/1982   Fed. Rep. of Germany.
2506910  12/1982  France.
2025586  1/1980   United Kingdom.

Primary Examiner—Henry Bennett
Attorney, Agent, or Firm—Hamilton, Brook, Smith & Reynolds

[57] ABSTRACT

In a water heating system, vapor in the products of combustion gases is condensed in a secondary heat exchanger positioned in a housing with the primary heat exchanger and combustion chamber. The two heat exchangers are coaxial coils with the secondary coil surrounding the primary. Gases flow radially through the primary coil, axially along a baffle and then axially through the secondary coil at an increased velocity. The gas/air mixture is burned in a burner within the primary heat exchanger and the gas product are drawn through the exchangers by a blower. A water storage tank is designed to enhance stratification of hot water over cooler water. The cooler water is used to condense vapor in the secondary heat exchanger.

10 Claims, 8 Drawing Figures

COMBUSTION PRODUCT CONDENSING WATER HEATER

RELATED APPLICATIONS

This is a continuation-in-part application to Ser. No. 150,289, 5-16-80, now U.S. Pat. No. 4,403,572 for Combustion Product Condensing Water Heater.

FIELD OF THE INVENTION

This invention relates to water heaters. More particularly, it relates to water heaters in which vapor in the products of combustion is condensed to retrieve latent heat of vaporization.

BACKGROUND

With the increasing cost of fuel, methods for increasing the efficiency of heat exchanger assemblies for extracting heat from the products of combustion of fuel burners has become increasingly more cost effective. One means of increasing the efficiency of heat recovery has been to burn the fuel in small-volume, water-walled combustion chambers. Forced draft or pulsed combustion techniques are utilized to achieve high rates of heat transfer and to vent the products of combustion.

Recently, systems have beeen proposed to cool the products of combustion below the dew point temperature of those products typically below 130° F., in order to condense some of the vapor and thereby extract the latent heat of vaporization of that vapor. To cool the products of combustion to that extent and to minimize the size, and thus the cost, of the heat exchanger assemblies, efficient heat exchangers must be designed.

An object of this invention is to provide an efficient water heating system in which heat is extracted from the products of combustion by condensing vapor in the products, the system having an acceptable size and cost.

The condensate from natural gas combustion products is mildly acidic, and the acidic nature of the condensate is expected to be a potential cause of corrosion. The acidic nature of the condensate may result from sulfuric acid, nitric acid, and carbonic acid.

A further object of this invention is to provide a water heating system designed to withstand the corrosive effects of the condensate at a minimal cost.

DISCLOSURE OF THE INVENTION

In a heating assembly of this invention, primary and secondary heat exchangers and a combustion chamber are positioned within a single housing. The combustion chamber is defined by the primary heat exchanger. The combustion products flow through the primary heat exchanger at a sufficiently low velocity to keep the temperature of the heat exchanger walls at an acceptable level. The products of combustion are then directed into a secondary heat exchanger in which the velocity of the products of combustion is increased in order to increase the heat transfer coefficient of that heat exchanger. Cold water flows through the secondary heat exchanger in counter flow relationship with the combustion gases to cool those products to a temperature below the dew point temperature. Vapor in the products of combustion is thereby condensed. After being heated in the secondary heat exchanger, the water is mixed with hot water from the output of the primary heat exchanger and the water mixture is directed through the primary heat exchanger at a higher flow rate than in the secondary heat exchanger. The hot mixture of water entering the primary heat exchanger assures that no condensation of the products of combustion occurs at this heat exchanger.

In the preferred water heating assembly, the primary heat exchanger is a coil of tubing which defines the combustion chamber. Products of combustion flow radially through that coil. The secondary heat exchanger is a second coil of tubing coaxial with and surrounding the first. Products of combustion flow through that coil axially at a higher velocity. A baffle directs products of combustion axially from the primary heat exchanger coil to an end of the secondary heat exchanger coil.

Prior to combustion, the combustion air and fuel may be preheated by combustion products in a tertiary heat exchanger which receives those products from the secondary heat exchanger.

In a system in which hot water is stored in an insulated storage tank, cool water is taken from the bottom of the tank and introduced into the burner and heat exchanger assembly, and the heated water is returned to an upper section of the storage vessel in such a manner as to avoid mixing of the heated water with the cooler water in the bottom of the vessel.

The preferred system utilizes a blower downstream of the burner and heat exchanger assembly for inducing a draft to propel the products of combustion.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF PREFERRED EMBODIMENTS

Figure 1:
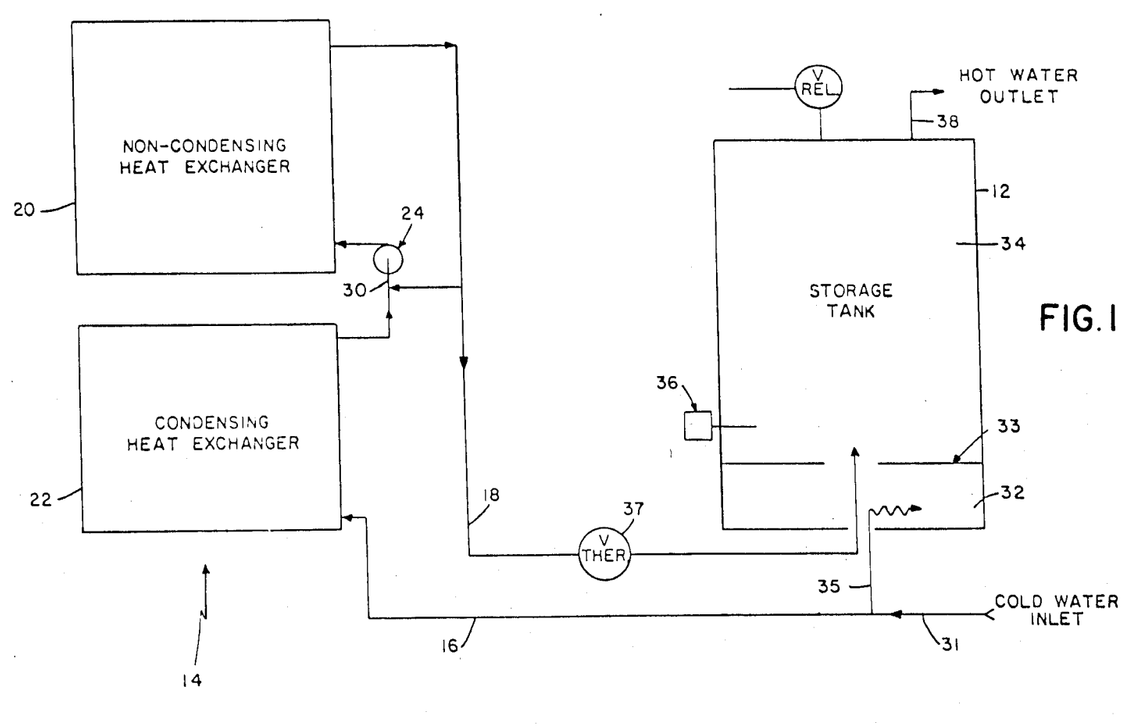
FIG. 1 is a block diagram of the water circuit of a preferred system embodying this invention.

A preferred system embodying this invention is shown schematically in FIG. 1. A storage tank 12 is connected to an external gas-fired water heater 14 by supply and return pipes 16 and 18. The water heater 14 comprises a primary, fired heat exchanger assembly 20 and an economizer 22 which is a secondary heat exchanger operating in the condensing mode. A circulating pump 24 placed between the economizer and the primary heat exchanger draws water from the return line 18 and from the economizer 22 and drives that mixture through the primary heat exchanger 20.

The storage tank is designed to maximize stratification between a small volume 32 of relatively cool water in the bottom of the tank and a larger volume 34 of stored hot water. In this case, the two volumes are separated by baffles 33. Typically the cool volume 32 is about 20 percent of the total tank volume. If hot water is taken from the outlet 38 of the storage tank while the heater 14 is in the standby mode, cold water is introduced into the lower volume 32 through a diffuser from a cold water inlet 31 and pipe 35.

When the heater assembly 14 is turned on, water is drawn from the lower volume 32 through pipe 16 if no water is being extracted through outlet 38; or a mix of water from the cold water inlet 31 and the lower volume 32 is drawn through pipe 16 if water is being extracted from the outlet 38. Water heated in the heater assembly 14 is returned through pipe 18 to the upper volume 34 in the storage tank 12. The baffles 33 inhibit mixing of the hot water from pipe 18 with the cooler water in the volume 32.

The cool water introduced into the economizer 22 through pipe 16 passes in counter flow heat exchange relationship with products of combustion which have already been cooled somewhat in the primary heat exchanger 20. The products of combustion and the water are sufficiently cool when introduced into the economizer 22 that the temperature of the products of combustion within the economizer is below the dew point temperature. This results in condensation of vapor in the products of combustion, and the latent heat of vaporization is transferred to the water in the economizer.

Water which has been preheated in the economizer 22 is introduced into the primary heat exchanger 20 which defines a combustion chamber. There the water is heated to the high temperature necessary for heating the water in the storage tank 12.

The purpose of the cold volume 32 should now be apparent. It provides a sufficiently large reservoir of cool water to enable the economizer to operate in the condensing mode throughout the on-cycle even when no cold water is drawn through the inlet 31 during the heating cycle. The volume of cool water should be minimized to reduce standby losses from and to limit the size of the storage tank. To that end, the cool water is rationed to the heater 14 at a low flow rate to condense vapor in the exhaust gas with a minimal amount of water.

The percentage of the storage tank which must be devoted to the volume of cooler water 32 can be determined from the following equation:

$$\frac{V_H}{V_C} = \frac{T_R - T_{cut-in}}{T_{Diff}}$$

Where $V_H$ and $V_C$ are the respective hot and cool volumes 34 and 32, $T_R$ is the temperature of the water in return line 18, $T_{cut-in}$ is the temperature of water in the storage tank at which the water heater is fired, and $T_{Diff}$ is the differential between the thermostat cut-in and cut-off temperatures. Typically, $T_R - T_{cut-in}$ is in the range of 40° to 50° F. To minimize standby losses and total tank volume, then volume $V_C$ should be less than 20 percent of the total tank volume. Thus, the thermostat differential temperature must be less than about 10° F. A temperature differential of 5° to 10° F. and a cool volume of 10 to 20 percent of the total tank volume are reasonable. For a given burner input, the flow rate through the heater can be controlled by a thermostatic valve 37 to maintain the desired return temperature. Alternatively, the flow rate might be held constant and the burner input varied, to maintain the steady return temperature.

Figure 8:
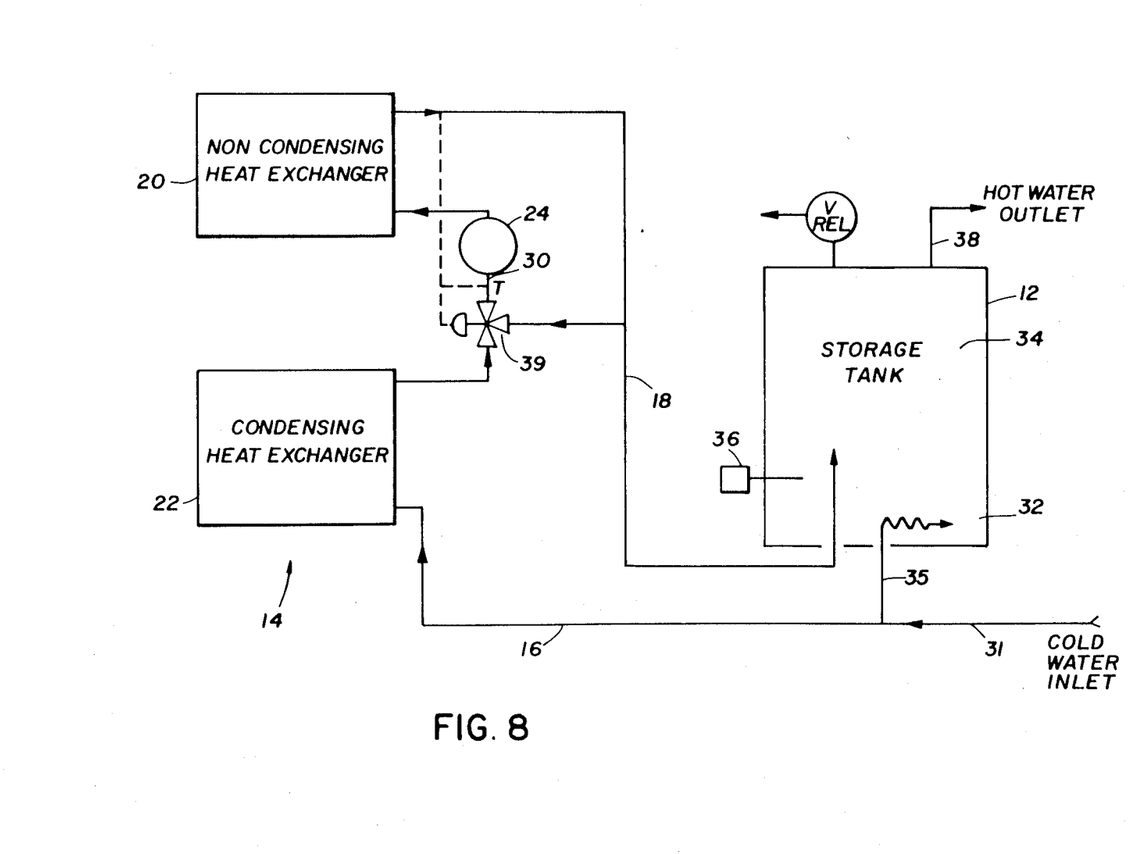
FIG. 8 is a block diagram of an alternative system embodying this invention.

A preferred method of controlling the flow rate through the heater is illustrated in FIG. 8. A thermostatic tempering valve 39 mixes cool water from the outlet of condensing heat exchanger 22 with water recirculated from the outlet of non-condensing heat exchanger 20 to maintain a fixed temperature at inlet 30 to pump 24, as illustrated in FIG. 8. The tempering valve is preferably of the type that varies the throttling of one stream in an opposite sense to the variation in throttling of the other stream. An example is Model N170 manufactured by Watts Regulator Company. It produces roughly constant flow rate through the non-condensing heat exchanger 20 and therefore a roughly constant output temperature if the inlet temperature at pump inlet 30 is held constant. Alternatively, the tempering valve may be controlled by a thermostatic bulb sensing the outlet temperature from non-condensing heat exchanger 20, in which case the inlet temperature to non-condensing heat exchanger 20 will also remain roughly constant.

Placement of pump 24 between primary heat exchanger 20 and the secondary heat exchanger 22 is important for the following reason. Hot water from the outlet 28 of the primary heat exchanger is recirculated back to the inlet 30 to raise the water inlet temperature of that heat exchanger above the dew point temperature of the products of combustion. This is done to prevent condensation in the primary heat exchanger. To minimize the cost of the system, the primary heat exchanger is not protected against corrosion by flue gas condensate.

A further advantage of recirculating water through the primary exchanger is that it increases water flow rate and thus establishes high water-side heat transfer coefficients. This minimizes liming of the main heat exchanger coil. This is unnecessary in the economizer due to the significantly lower heat fluxes and water temperatures in the economizer section.

The operating principle is best illustrated by the following example: Consider a 100 gallon tank with a thermostat that operates over a 10° F. differential and is located one fifth of the way from the bottom of the tank. Assume that the lower section 32 of the tank contains 20 gallons of water at an average temperature of 80° F., and that the average storage temperature is 140° F.

In the proposed concept, the water heater would use the 20 gallons of cooler water to heat 80 gallons of stored water from 135° F. to 145° F. During this process, the cooler water would be displaced by 135° F. water. A heat balance indicates that the total energy required is 15,700 Btu. If the heat output of the water heater is 157,000 Btu/hr, then the burner-on time is 6 minutes. In this case, the circulating pump 24 would draw water at the rate of 3.33 GPM from the bottom section and would return it to the top section at a temperature of 175° F. At the end of the on-cycle, the mixed temperature of the upper section will have reached 145° F., and the bottom section will contain water at 135° F. The flow control is preferably accomplished by thermostatic control of the return temperature to the tank by a valve 37 as this will prevent excessive temperatures if the bottom temperature, and thus the heater inlet temperature, gets too high. Alternatively, the desired flow rate may be set by a constant flow regulator or by a fixed orifice.

A variation of the concept might include the use of a separate, smaller preheat tank instead of the integral volume 32.

Figure 2:
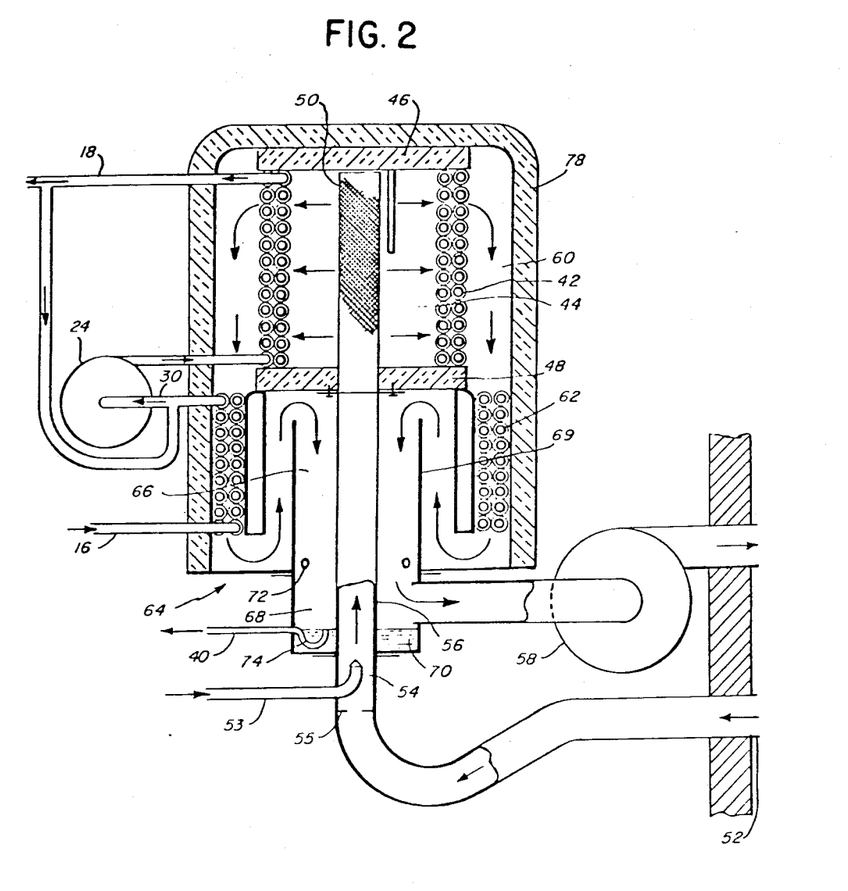
FIG. 2 is an elevational cross sectional view of a preferred embodiment of the burner and heat exchanger assembly embodying this invention.

One preferred design of the water heater 14 is shown in FIG. 2. The primary heat exchanger consists of an integrally finned copper tube coil 42 surrounding the combustion chamber 44. This arrangement provides an efficient "water-wall" combustion chamber which minimizes combustion chamber heat losses and requires a minimal amount of refractory insulation 46 and 48. Moreover, with radial flow through the coil, the large area of the coil facing the combustion chamber provides relatively low gas velocities. Such low gas velocities are necessary to prevent excessive wall temperatures due to the high temperature of the combustion products.

A mixture of natural gas and air is burned at a burner 50 within the combustion chamber. In a pipe 56 combustion air from an exterior inlet 52 is mixed with natural gas from a pipe 53 and nozzle 54. The desired air flow rate is established by fixed orifice 55. The mixture is drawn into the combustion chamber by a blower 58 positioned in the flue gas outlet. Alternatively, the mixture can be propelled by a blower placed upstream of the burner.

Combustion gases are collected in an exhaust annulus 60 before passing through the economizer coil. The gas temperature at the annulus is in the range of 200° to 400° F.

The combustion products are cooled further in the economizer coil 62 which is designed for condensing operation. Because of the corrosive properties of the condensate, the economizer is made of a corrosion-resistant material, such as 70/30 cupro-nickel or stainless steel. The economizer is designed for cross-counterflow of the combustion products. With axial flow of gases through this coil, the combustion products flow at high velocities in order to achieve high heat transfer coefficients. Here, high gas-side transfer coefficients can be utilized without fear of excessive wall temperatures because both the gas and water temperatures are much lower than in the main heat exchanger. Most of the product of combustion pressure drop will occur in this section FIG. 2 also illustrates an optical third heat exchanger section 64. This is a counterflow pre-heater which uses the latent and sensible heat of the exhaust products to preheat the incoming gas/air mixture. The preheater 64 is a compact arrangement positioned concentrically within the economizer coil 62. Exhaust gas which has passed through the economizer is directed up through a first annulus 66 and then back down through a second annulus 68. The annuli are separated by a cylinder 69. Gas in the annulus 68 is in counter flow heat exchange relationship with the incoming mixture of natural gas and air. Any liquid which condenses from the exhaust gases in this preheater is collected in a reservoir 70. Also, any condensed liquid from the economizer 62 flows through holes 72 in the cylinder 69 into that same reservoir. The collected liquid is taken off through an anti-syphon tube 74 to the drain pipe 40. The anti-syphon tube insures that exhaust gas can not leak into the surrounding area but allows condensate to be drained from the heater.

With sufficiently low incoming water temperatures, the preheater 64 is probably unnecessary, since it will add less than 1% to the recovery efficiency. However, when incoming water temperatures are high, as may occur in a hot water booster, the air preheater may produce worthwhile savings. The heat that can be recovered in this type of preheater is limited by the heat capacity of the incoming mixture. Typically, preheating the inlet mixture by 100° F. would increase efficiency by approximately 2.5%.

Losses in the system are minimized through the use of several design features. The combustion chamber is small and does not have a large inactive surface exposed to flame temperatures. The first stage heat exchanger is small with little water inventory. The bottom surface of the combustion chamber forms the top of the air preheater, so that heat losses in this direction will reenter the exhaust stream and increase the heat recovered in the preheater. Insulation is shown on this surface only for the protection of the metal surface which forms the bottom of the combustion chamber. This insulation may be eliminated if the exhaust gas can be utilized to cool this surface. The main "radiation" heat loss occurs through the top of the combustion chamber and along the outside shroud which contains the exhaust gas. Both these surfaces are insulated with insulation 78 to minimize these losses. The exhaust gas is relatively cool by the time it reaches the bottom of the unit and this surface need not be insulated.

Other significant features include the use of an induced draft blower which causes the unit to operate under negative draft conditions; thus, sealing the heater is not as critical as it would be if the unit were pressurized. Also since the exhaust gas is cool at this point, a plastic blower may be used to reduce costs and improve performance over a sheet metal blower.

The unit is shown using sealed combustion; that is, combustion air is drawn directly from the building exterior and exhaust gas is blown directly to the exterior. A natural convection stack is not feasible because of the low exhaust temperature. An alternative is the use of a conventional air intake plus exhaust through plastic pipe installed as a roof vent or through an unused chimney.

Figure 3:
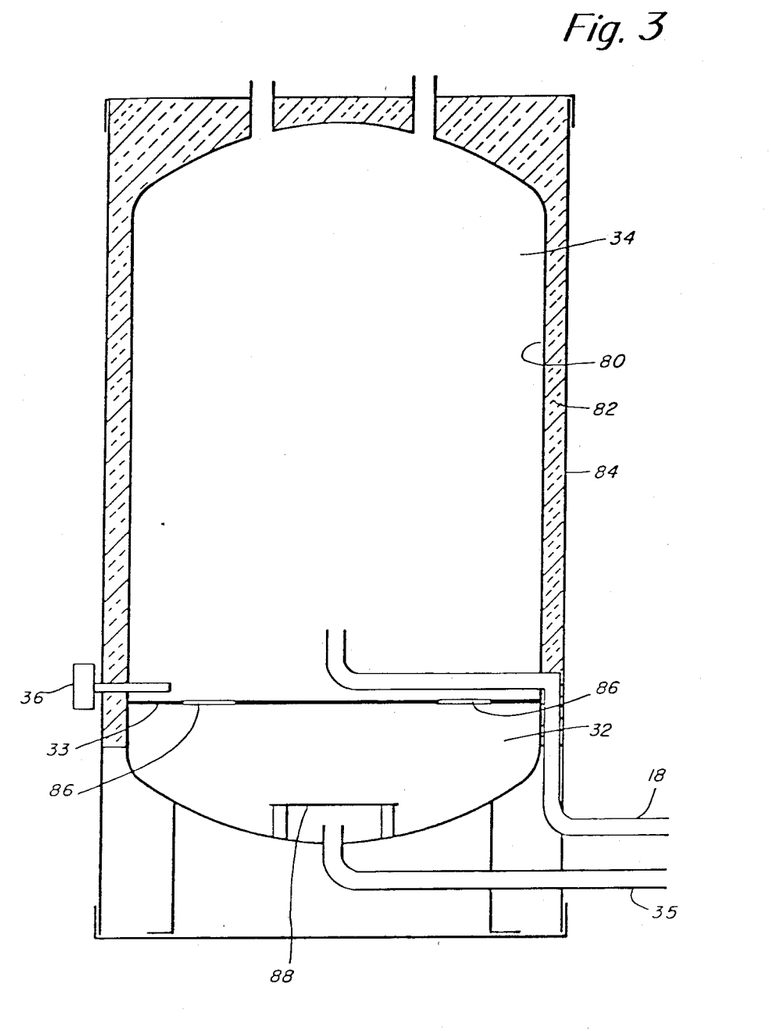
FIG. 3 is an elevational cross sectional view of a possible storage tank configuration for use with this invention.
Figure 4:
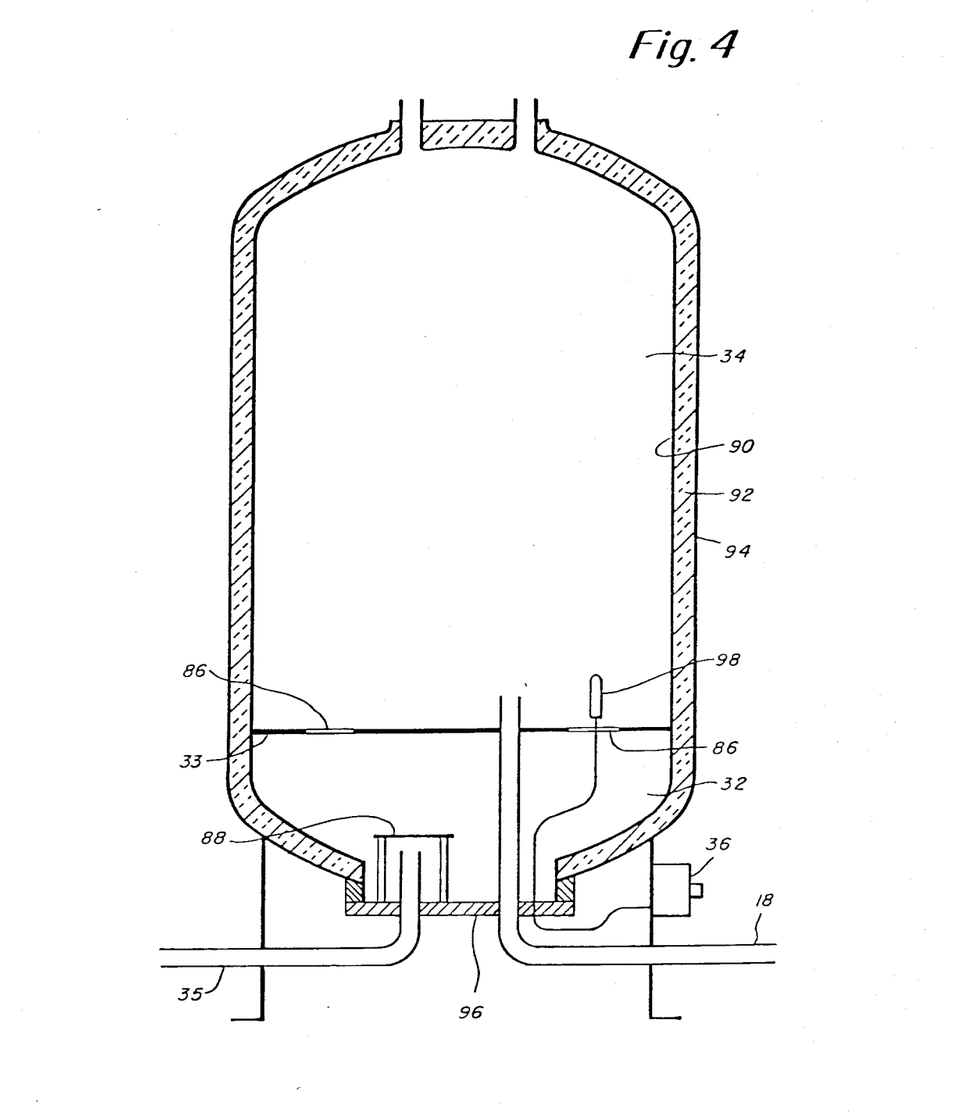
FIG. 4 is an elevational cross sectional view of an insulated plastic lined storage tank for use in this invention.

Alternative storage tanks are illustrated in FIGS. 3 and 4. The tank of FIG. 3 is conventional, with the exception of the provisions for stratification described above. This tank is a glass lined steel tank 80 surrounded by insulation 82 and a metal housing 84. The hot return pipe 18 enters through the side of the tank and directs the hot water upwardly into the upper volume 34. The baffle 33 is positioned below the hot return pipe 18 to assist in the natural stratification of the hot and cool water within the tank. Holes 86 in the baffle allow for displacement of water through the baffle as necessary. A diffuser 88 is positioned over the inlet pipe 35 so that flow between the volumes 32 and 34 is not induced by introduction of cold water into the tank. A thermostat 36 controls the operation of the heater.

An alternative version of the tank is illustrated in FIG. 4. This tank structure includes a plastic lining 90 surrounded by insulation 92, such as foam insulation, and an outer steel tank 94. All connections to the interior of the tank are through a bottom plate 96. This arrangement includes the baffle 33 and the diffuser 88 as in the embodiment of FIG. 3. The thermostat 36 is also connected through the bottom plate 96 to a remote sensing bulb 98.

It should be noted that the baffle 33 is not absolutely necessary. It may be sufficient to have the hot return pipe outlet positioned sufficiently high within the tank that a lower volume of cool water remains. Also, flow directors may be mounted directly to the outlet of pipe 18 to avoid the need for a baffle 33 fabricated within the storage tank.

Figure 5:
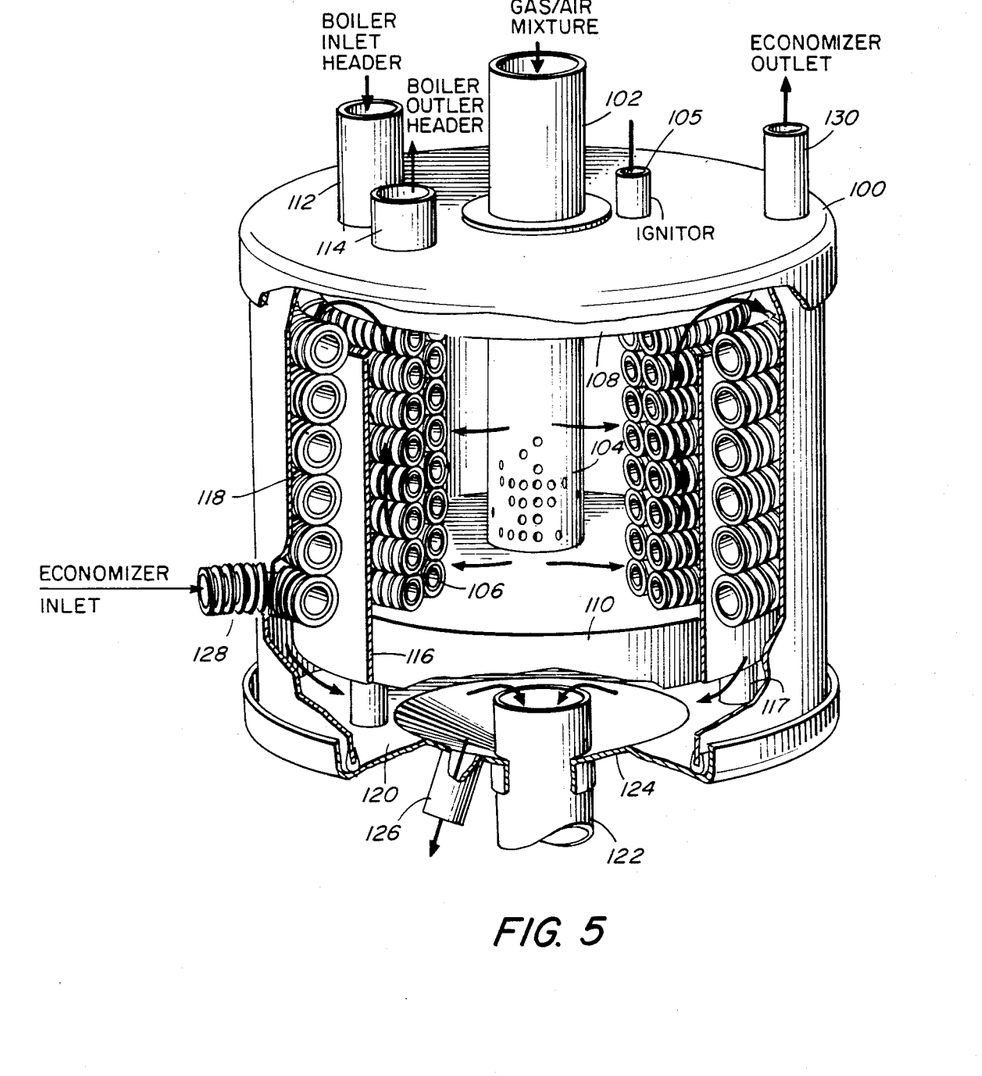
FIG. 5 is a perspective view of an alternative embodiment of the burner and heat exchanger assembly, broken away to show the details of the heat exchanger assembly.

FIG. 5 illustrates a more compact embodiment of the burner and heat exchanger assembly. In this arrangement, the secondary, economizer heat exchanger coil surrounds the primary, boiler heat exchanger coil, and the two are separated by a coaxial baffle. A tertiary heat exchanger is not utilized.

The embodiment of FIG. 5 includes a cylindrical housing 100. The premixed gas and air mixture is introduced through a conduit 102 along the central axis of that housing through the top thereof. As before, a perforated, cylindrical flameholder 104 is positioned centrally within the housing. The flame may be ignited by means of an electric igniter 105. Also as before, the combustion chamber is a water-walled combustion chamber defined by the primary heat exchanger coil 106. The coil 106 is sandwiched between refractory insulating layers 108 and 110.

Figure 6:
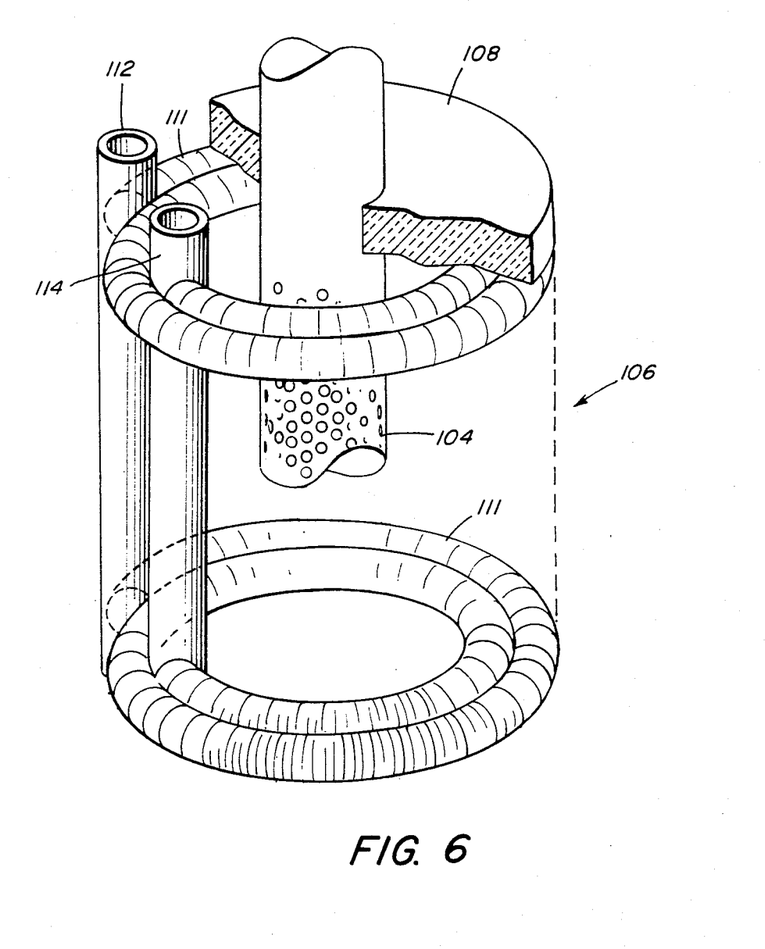
FIG. 6 is a perspective illustration of the primary heat exchanger coil of the embodiment of FIG. 5.
Figure 7:
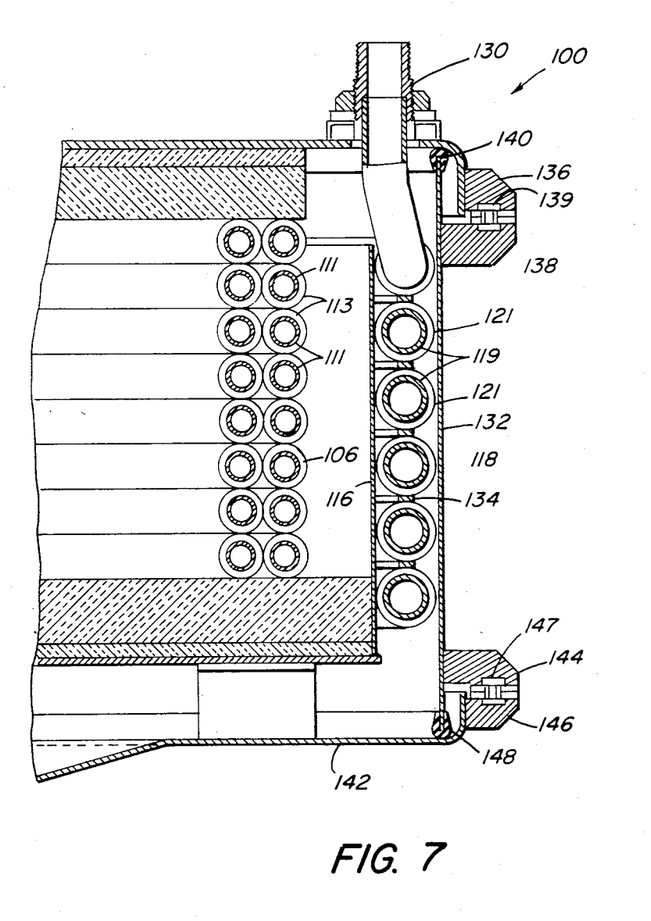
FIG. 7 is a partial, enlarged, elevational cross section of the right side of the assembly of FIG. 5.

The primary heat exchanger coil and its inlet and outlet headers are better illustrated in FIG. 6. A series of finned tubes 111 are welded or brazed to a tubular inlet header 112. The fins 113 on the tubes 111 are best shown in FIG. 7. The tubes encircle the flameholder 104, pass between the inlet header 112 and the outlet header 114 and again encircle the flameholder 104 before joining the outlet header 114. Products of combustion flow radially through this primary heat exchanger coil at a relatively low velocity as in the prior embodiment.

After passing through the primary heat exchanger coil, the products of combustion are directed axially behind that coil by a coaxial baffle 116 (FIGS. 5 and 7). The baffle 116 is surrounded by the coaxial secondary heat exchanger coil 118, and the products of combustion flow at an increased velocity axially past that coil between the baffle and the outer housing 100.

The cooled combustion products leave the secondary heat exchanger at about 100°-130° F. The coil 118 is formed of a single tube 119 having fins 121. They collect in a plenum 120 below the insulation 110 and are exhausted through the exhaust flue 122. As before, vapor in the products of combustion is condensed. That vapor is collected in the plenum and drained to a condensate sump 124 from which it can be drained through the port 126.

Cool water is introduced to the secondary heat exchanger through the inlet 128. The preheated water is taken from the outlet 130 and directed to the boiler inlet header 112 by a pump as in the system diagram of FIG. 1. The heated water from the outlet header 114 is partially recirculated by the pump and partially returned to the volume of hot water in the storage tank as shown in the system diagram of FIG. 1.

The assembly is constructed such that the flameholder 104, the primary, boiler heat exchanger coil 106 and secondary, economizer heat exchanger coil 118 are suspended from a top plate 130 of the housing 110 as shown in FIG. 7. The cylindrical outer skin 132 of the housing is wrapped around the secondary heat exchanger coil and tightened with drawbolts (not shown) to form a snug fit over the coil. Spacer strips on the economizer coil leave a small gap of about 0.030 inch between the sides of the coil and the outer wrap. The close fit of the inner cylindrical baffle and the outer wrap 132 with respect to the coil 118 is an important factor in controlling the velocity of the combustion products over the coil. The individual turns of the coil are spaced by spacers 134.

As shown in FIG. 7, the outer skin 132 is joined to the top 130 by brackets 136, 138 and bolts 139. A seal is made by an elastomeric or heat resistant fibrous gasket material 140. The condensate sump and the bottom 142 of the housing are fixed to the lower insulator 110 and the baffle 116 by struts 117. That assembly is joined to the cylindrical skin 132 by brackets 144 and 146. A gasket 148 is provided to form the seal.

The bottom assembly, including the baffle 116, can be removed by dropping it from below the overall assembly to expose the flameholder and boiler coils. Further, the skin 132 can be removed to further expose the economizer coil and the boiler coils.

Because of its very compact structure, the embodiment of FIGS. 5-7 has significantly less heat loss, since the outer skin is at a substantially lower temperature than was the boiler skin in the embodiment of FIG. 2 and because the total surface area is significantly less.

We claim:

1. A water heating assembly comprising:
   a generally cylindrical housing;
   a fuel burner within the housing at about the center axis of the housing;
   a primary heat exchanger coil within the housing, surrounding the fuel burner, coaxial with the housing, the coil being closed at each end such that combustion gas from the burner flow radially therethrough;
   a combustion gas impermeable baffle within the housing, coaxial with the housing, surrounding and spaced from the primary heat exchanger the space between the primary heat exchanger and the baffle being closed at one end to axially direct combustion gas from the primary heat exchanger coil to the opposite end of the baffle; and
   a second heat exchanger coil within the housing connected in series with the primary heat exchanger coil, coaxial with the housing, surrounding the baffle such that combustion gas from the primary heat exchanger flows around said opposite end of the baffle and axially past the secondary heat exchanger coil.

2. A water heating assembly as claimed in claim 1 wherein the primary heat exchanger and secondary heat exchanger are mounted to a first end section of the cylindrical housing and the baffle is mounted to a second end section of the cylindrical housing, the second end section being removable from the first end section.

3. A water heating assembly as claimed in claim 1 wherein the primary heat exchanger, the secondary heat exchanger, and the fuel burner are suspended from an upper end section of the cylindrical housing and the baffle and a sump are supported by a lower end section of the cylindrical housing, and the second end section is removably suspended from the upper end section.

4. A water heating assembly comprising:
   a heat exchanger and combustion chamber housing;
   a water-walled combustion chamber within the housing defined by a primary heat exchanger coil closed at each end, the products of combustion gas flow path past the primary heat exchanger coil being radial and providing a first gas velocity through the primary heat exchanger;

a secondary heat exchanger coil within the housing, coaxial with and surrounding the primary heat exchanger coil, for receiving gases cooled by the primary heat exchanger, the second heat exchanger coil providing for a second combustion gas velocity substantially greater than the first;

a combustion gas impermeable baffle between the primary and secondary coils for directing combustion gases from the primary heat exchanger coil axially to an end of the second heat exchanger coil for flow axially past the secondary heat exchanger coil;

a cool water inlet;

means for circulating cool water from the cool water inlet through the secondary heat exchanger in counter-flow heat exchange relationship with the combustion gases to cool the gases below their dew piont temperature and condense water vapor from the gases; and means for mixing water from the secondary heat exchanger with a portion of the water from the output of the primary heat exchanger and for directing the water mixture through the primary heat exchanger to cool the combustion gases to a temperature which is above their dew point temperature.

5. A water heating assembly as claimed in claim 4 wherein the flow of the gas/air mixture into the burner is induced by a blower positioned downstream from the secondary heat exchanger.

6. A water heating system as claimed in claim 4 wherein a water storage assembly including a volume of hot water and a smaller volume of cooler water in communication with the hot water, said cool water inlet being in fluid communication with said volume of cooler water, and heated water from said primary heat exchanger is returned to said volume of hot water in such a manner as to avoid mixing with water in said volume of cooler water.

7. A water heating system as claimed in claim 6 wherein the water storage assembly is a tank separated into hotter water and cooler water volumes by a baffle.

8. A water heating system as claimed in claim 6 further comprising a diffuser positioned over a cold water inlet into the bottom of the tank.

9. A water heater assembly as claimed in claim 1 wherein the flow of water through the secondary heat exchanger and the flow of water recirculating through the primary heat exchanger are controlled by a thermostatic tempering valve means in order to maintain a predetermined temperature at the inlet of the primary heat exchanger.

10. A water heater assembly as claimed in claim 1 wherein the flow of water through the secondary heat exchanger and the flow of water recirculating through the primary heat exchanger are controlled by thermostatic mixing valve means to maintain a predetermined temperature at the outlet of the primary heat exchanger.

* * * * *